United States Patent [19]
Jonsson et al.

[11] Patent Number: 5,352,183
[45] Date of Patent: Oct. 4, 1994

[54] ILEAL RESERVOIR DEVICE

[75] Inventors: Olof Jonsson, Västra Frölunda; Bo Rangert, Mölnlycke; Staffan Akerlund, Göteborg, all of Sweden

[73] Assignee: Nobelpharma AB, Goteborg, Sweden

[21] Appl. No.: 987,969

[22] Filed: Dec. 11, 1992

[30] Foreign Application Priority Data

Dec. 12, 1991 [SE] Sweden .............................. 9103668-1

[51] Int. Cl.$^5$ .............................................. A61F 2/02
[52] U.S. Cl. ......................................... 600/32; 600/29
[58] Field of Search ..................................... 600/29-32; 606/152-158; 128/DIG. 25

[56] References Cited

U.S. PATENT DOCUMENTS

| | | | |
|---|---|---|---|
| 4,217,664 | 8/1980 | Faso | 606/156 |
| 4,553,542 | 11/1985 | Schenck et al. | 606/152 |
| 4,773,393 | 11/1988 | Habes et al. | 128/DIG. 25 |
| 4,905,693 | 3/1990 | Ravo | 606/153 |
| 4,969,902 | 11/1990 | RAvo | 128/DIG. 25 |

FOREIGN PATENT DOCUMENTS

| | | | |
|---|---|---|---|
| 0614844 | 5/1935 | Fed. Rep. of Germany | 606/158 |
| 0516401 | 6/1976 | U.S.S.R. | 606/153 |
| 1621897 | 1/1991 | U.S.S.R. | 606/156 |

OTHER PUBLICATIONS

Urinary diversion via a continent ileal reservoir: Clinical results in 12 patients, N. G. Kock, A. E. Nilson, L. J. Norlen and B. M. Philipson; The Journal of Urology, vol. 128, Sep. 1982.

Current status of the Ileal Reservoir for Continent Urinary Diversion, N. G. Kock, L. Norlen, B. M. Philipson and S. Akerlund; Surgical Rounds, Jan. 1985, pp. 32–48.

Primary Examiner—Randall L. Green
Assistant Examiner—Rob Clarke
Attorney, Agent, or Firm—Pollock, Vande Sande & Priddy

[57] ABSTRACT

A device for stabilizing the base of the nipple valves in a continent ileal reservoir with inlet and outlet nipple valves, includes a substantially annular member made of a biocompatible material, the annular member being pre-formed and permanently shaped to substantially define a ring. The ring has a radial slot formed therein to allow insertion of the annular ring member over the base of a respective nipple valve, with the annular ring member having an inner radius adapted to fit around said base. The annular ring member has first and second surfaces, with one of the surfaces facing the ileal reservoir outer wall, and through holes extending through said first and second surfaces for promoting a good adherence of the device to the surrounding soft tissue.

6 Claims, 1 Drawing Sheet

ILEAL RESERVOIR DEVICE

FIELD OF THE INVENTION

The present invention relates to a device for stabilizing, the base of the nipple valves in a continent ileal reservoir (Kock-pouch) for urinary diversion.

BACKGROUND OF THE INVENTION

Urinary diversion via a continent ileal reservoir in the abdominal cavity has been previously performed, see for instance:

(I) Urinary diversion via a continent ileal reservoir: Clinical results in 12 patients, N. G. Kock, A. E. Nilson, L. O. Nilsson, L. J. Norlén and B. M. Philipson; The Journal of Urology, Vol. 128. Sept 1982, and (II) Current Status of the Ileal Reservoir for Continent Urinary Diversion, N. G. Kock, L. Norlén, B. M. Philipson and S. Åkerlund: Surgical Rounds, Jan. 1985, p. 32–48.

For construction of the ileal reservoir (Kock reservoir) a small bowel segment is isolated from the intestinal canal and used for the reservoir walls. The operative technique for this is previously known, see ref. I–II, and will therefore not be described in detail here.

The completed ileal reservoir is made with a reflux valve nipple (inlet opening) and a continence valve nipple (outlet opening). Both these valves are formed by a surgical technique in which an ileum segment is folded into a U-shape directed towards the interior of the reservoir and preformed into small inlet and outlet channels. Also the technique for forming these nipple valves is described in the references I–II.

The position and form of the valve nipples are not always maintained, however. In the long run an eversion and relapse may occur which means a malfunction of the valve nipples with respect to the inlet and outlet control of the reservoir.

In order to prevent such eversion of the valve nipples it is previously known to stabilize the valve nipples by means of staples applied by a stapling instrument so that the folded tissue is clamped together. The staples can be made of an absorbable or biocompatible material such as titanium. The valve nipples are secured by such staples, but as the staples penetrate the reservoir wall it involves a risk for the formation of stones in the urine when the contents of the reservoir is infected. Furthermore it is an expensive method as four rows of staples are applied around the nipple valve by use of a specific stapling instrument having fastener and retainer parts as well as a loading unit for the staples.

It is also previously known to stabilize the valve nipples by means of a Marlex mesh, that is, a strip of a synthetic mesh-like material positioned around the base of the nipple valves and sutured together to prevent desusception of the nipple valves but not so tight that urinary flow is obstructed. The Marlex mesh strips are applied exterior to the reservoir around the base of the nipple valves. However, the Marlex mesh may still irritate the surrounding tissue and cause fistulation and later on formation of stones in the urine.

SUMMARY OF THE INVENTION

The object of the present invention is to provide a device for stabilizing the base of the nipple valves in a continent ileal reservoir without the present above-mentioned drawbacks.

According to the invention the device consists of a preformed, shape permanent, slotted ring made of a biocompatible material applied exterior to the reservoir around the base of the nipple valve.

The ring is preferably made of titanium and provided with holes to allow ingrowth of the surrounding soft tissue thereby providing a mechanical interlocking the holes are also used for suturing the ring.

The ring is preferably disc-shaped to increase contact surface to the abdominal wall as well as to the ileum wall tissue. A disc-shaped ring can more easily be adapted to the wall of the reservoir and counter-balance the pressure from the reservoir wall. Furthermore it can be formed to suit the individual reservoir form and provide a good support in the right position.

Compared to the Marlex mesh the present device provides a preformed ring, having a rigid construction, which can be formed to a certain extent, but with a geometry adapted to the base of the nipple valve. The diameter of the ring is preferably in the interval of 20–30 mm.

In the following a preferred embodiment of the invention will be described more in detail with reference to the accompanying drawings, in which:

DETAILED DESCRIPTION OF THE PREFERRED EMBODIMENT

Figure 1:
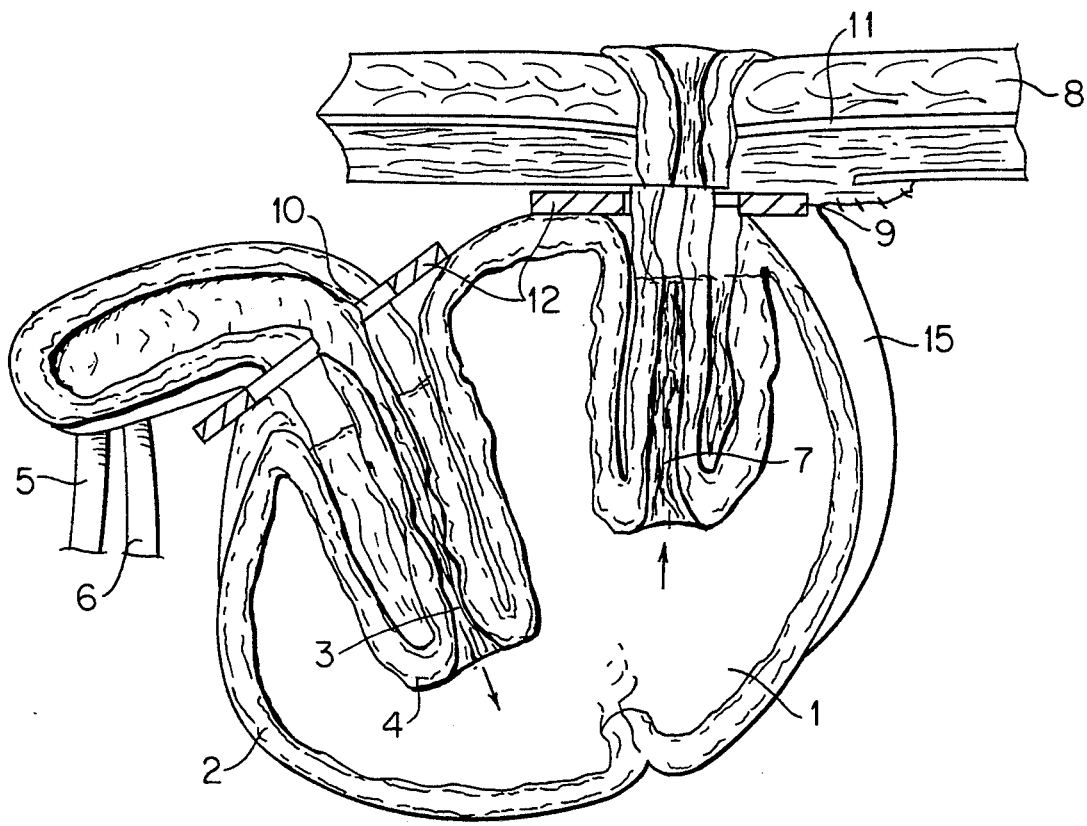
FIG. 1 illustrates a completed ileal reservoir having two annular discs according to the present invention applied around the base of the nipple valves.

FIG. 1 shows a completed continent ileal reservoir according to Kock as illustrated in the references I–II. The reservoir has been created by means of an ileum segment which has been re-constructed to a bladder substitute 1. The wall 2 of the reservoir therefore consists of ileal tissue.

The reservoir has an inlet channel 3, a so-called reflux nipple valve 4 made in the reservoir wall having a length of approximately 5 cm and directed towards the interior of the reservoir. The inlet 3 of the reservoir is connected to the upper urinary tract via the ureters 5, 6.

The outlet channel 7 of the reservoir, the so-called continent nipple valve, also comprises a construction made in the reservoir wall having a length of approximately 5 cm and directed towards the interior of the reservoir. The outlet channel is connected to an opening in the abdominal wall 8 for drainage of the reservoir by means of ureteral catheters (not shown).

As already mentioned the two nipple valves are pre-constructed by means of specific instruments. In order to avoid malfunction of the substitute bladder it is important to have a "low-pressure" reservoir for collection and storage of the urine. This is important in order to allow urinary flow from the upper urinary tract to the receptacle but also in order to minimize the forces acting on the valves providing continence and preventing reflux thereby decreasing the risk for desusception and other complications with respect to the valves. However, some kind of stabilizing means are required on the nipple valves in order to prevent the nipple valves from desusception due to long-term pressure on the reservoir wall. According to the present invention, therefore, a pre-formed slotted titanium rings 9 and 10 respectively, has been applied around the base of each nipple valve exterior the reservoir.

The titanium ring 9 applied around the outlet nipple valve has a surface 11 facing the abdominal wall and a surface 12 facing the ileal reservoir wall. The ring has been anchored by means of sutures but the titanium material also promotes soft tissue ingrowth onto the surface. The titanium ring has a comparatively large diameter, approximately 30 mm, to avoid obstruction of the catheterization.

The titanium ring 10 has a somewhat smaller diameter, approximately 24 cm, to prevent the formation of hernia, that is to prevent parts of the ileal wall from being squeezed through the center hole at the side of the nipple valve wall.

Figures 2A, 2B:
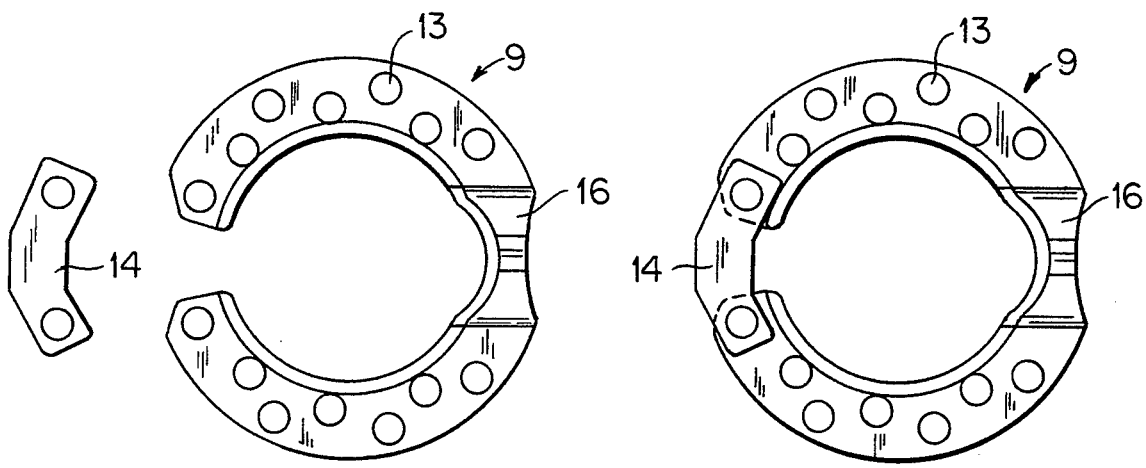
FIG. 2A shows an example of a ring to be used with the locking means removed from the ring.
FIG. 2B shows an example of a ring to be used with the locking means applied to the ring.

FIG. 2 shows an example of a titanium ring which can be used. Titanium is a biocompatible material which promotes a good adherence to the surrounding soft tissue without inflammatory complications. The ring has a number of soft tissue ingrowth holes 13 to provide also a mechanical interlocking of the ring to the surrounding tissue. The holes are also used for suturing the ring prior to the healing phase. The ring has an annular disc form for an increased surface contact with the surrounding abdominal and ileal walls. The ring is also open (slotted) so that it can be applied around the nipple valve. The ring has preferably locking means 14, also made of titanium, which are mounted on the ring after the ring has been disposed about the base of the nipple valve. The locking means prevents any relative movement between the two free ends of the ring and it also prevents tissue ingrowth in the opening between the two ends.

In order to prevent that the mesenatary, comprising vessels, nerves and connective tissue, is squeezed between the ring 9 and the abdominal wall 8 the ring is formed with a segment 16 cambered outwards.

Figure 3:
FIG. 3 shows some details of the different rings which can be used according to the present invention.

FIG. 3 is a sectional view of the titanium ring in which the inner circular boundary 17 has an L-shape form to reduce the risk of scraping and an unintentional penetration of the tissue surrounded by the ring.

We claim:

1. A device for stabilizing the base of the nipple valves in a continent ileal reservoir including inlet and outlet nipple valves, said device comprising:

a substantially annular member made of a biocompatible material, said annular member being pre-formed and permanently shaped to substantially define a ring, said annular ring member having a radial slot formed therein to allow insertion of said annular ring member over the base of a respective nipple valve, said annular ring member having an inner radius adapted to fit around said base, said annular ring member including an outwardly cambered segment so as to overbridge the mesentery, said annular ring member having first and second surfaces, one of said surfaces facing the ileal reservoir outer wall, said annular ring member being provided with means extending through said first and second surfaces for promoting a good adherence of said device to the surrounding soft tissue.

2. A device according to claim 1, wherein said biocompatible material is titanium.

3. A device according to claim 1 wherein said annular ring member is substantially disc-shaped and said first and second surfaces are dimensioned to provide increased surface area to promote said good adherence of said device to said surrounding tissue.

4. A device according to claim 3, wherein said means for promoting adherence includes a plurality of soft tissue ingrowth through holes provided in said surfaces.

5. A device according to claim 1, wherein said annular ring member is provided with locking means for closing off said slot after said ring has been inserted around the base of the nipple valve.

6. A device according to claim 1, wherein the inner periphery of said annular ring member includes an upstanding rim forming an L-shape with one of said surfaces.

* * * * *